United States Patent
Oh et al.

(10) Patent No.: US 12,315,153 B2
(45) Date of Patent: May 27, 2025

(54) APPARATUS AND METHOD FOR PREDICTING BIOMETRICS BASED ON FUNDUS IMAGE

(71) Applicant: KOREA UNIVERSITY RESEARCH AND BUSINESS FOUNDATION, Seoul (KR)

(72) Inventors: Jae Ryung Oh, Seoul (KR); Jae Ho Han, Seoul (KR); Yeon Woo Jeong, Seoul (KR); Bo Ram Lee, Seoul (KR)

(73) Assignee: KOREA UNIVERSITY RESEARCH AND BUSINESS FOUNDATION, Seoul (KR)

( * ) Notice: Subject to any disclaimer, the term of this patent is extended or adjusted under 35 U.S.C. 154(b) by 429 days.

(21) Appl. No.: 17/903,787

(22) Filed: Sep. 6, 2022

(65) Prior Publication Data

US 2023/0047199 A1    Feb. 16, 2023

Related U.S. Application Data

(63) Continuation of application No. PCT/KR2021/010766, filed on Aug. 12, 2021.

(51) Int. Cl.
*G06T 7/12* (2017.01)
*A61B 5/103* (2006.01)
*G06T 7/00* (2017.01)

(52) U.S. Cl.
CPC ............ *G06T 7/0012* (2013.01); *A61B 5/103* (2013.01); *G06T 2207/20081* (2013.01); *G06T 2207/30041* (2013.01); *G06T 2207/30101* (2013.01)

(58) Field of Classification Search
CPC ......... G06T 7/0012; G06T 2207/20081; G06T 2207/20084; A61B 5/103
USPC ......................................................... 382/128
See application file for complete search history.

(56) References Cited

U.S. PATENT DOCUMENTS

| | | | |
|---|---|---|---|
| 7,500,751 B2* | 3/2009 | Tajima | A61B 3/14 351/221 |
| 9,462,945 B1* | 10/2016 | Barriga | A61B 3/152 |
| 9,818,030 B2* | 11/2017 | Aoki | A61B 3/113 |
| 11,901,080 B1* | 2/2024 | Matt | G06T 7/0012 |
| 12,079,993 B1* | 9/2024 | Lochner | G16H 30/40 |
| 2013/0148081 A1* | 6/2013 | Tanaka | A61B 3/102 351/206 |

(Continued)

FOREIGN PATENT DOCUMENTS

| | | |
|---|---|---|
| CN | 110415245 | 11/2019 |
| JP | 2019005319 | 1/2019 |

(Continued)

*Primary Examiner* — William D Titcomb
(74) *Attorney, Agent, or Firm* — CANTOR COLBURN LLP

(57) ABSTRACT

Provided are apparatus and method for predicting biometrics using a fundus image. The method for predicting biometrics using a fundus image includes steps of preparation of a plurality of learning fundus images, generation of a learning model for predicting corresponding biometrics using the prepared data based on at least one characteristic of the fundus reflected in the prepared plurality of learning fundus images, reception of a prediction target of fundus image, and prediction of the biometrics of the subject of the prediction target of fundus image by using the generated learning model.

14 Claims, 6 Drawing Sheets

(56) References Cited

U.S. PATENT DOCUMENTS

| | | | | |
|---|---|---|---|---|
| 2014/0294235 A1* | 10/2014 | Ishida | .................. | G06V 40/193 |
| | | | | 382/103 |
| 2017/0112372 A1* | 4/2017 | Chakravorty | ......... | G06T 7/0012 |
| 2017/0156582 A1* | 6/2017 | Ehlers | .................... | G16H 50/30 |
| 2018/0140180 A1* | 5/2018 | Coleman | ............... | G06T 7/0012 |
| 2019/0110753 A1* | 4/2019 | Zhang | .................. | A61B 3/0025 |
| 2019/0365314 A1* | 12/2019 | Shiba | .................... | A61B 5/1075 |
| 2020/0375521 A1* | 12/2020 | Hadoux | ................ | G01N 21/31 |
| 2021/0219839 A1* | 7/2021 | Kim | .......................... | G06T 7/70 |
| 2021/0228073 A1* | 7/2021 | Park | ....................... | G16H 50/20 |
| 2021/0319556 A1* | 10/2021 | Chauhan | ............... | G06T 7/0014 |
| 2021/0319558 A1* | 10/2021 | Min | ........................ | A61B 8/12 |
| 2022/0160228 A1* | 5/2022 | Leahy | .................. | A61B 3/0025 |
| 2023/0036463 A1* | 2/2023 | Yang | ........................ | G06T 7/12 |

FOREIGN PATENT DOCUMENTS

| | | |
|---|---|---|
| KR | 20190087272 | 7/2019 |
| KR | 20190089471 | 7/2019 |
| KR | 20200005407 | 1/2020 |

* cited by examiner

APPARATUS AND METHOD FOR PREDICTING BIOMETRICS BASED ON FUNDUS IMAGE

BACKGROUND

Field

The present disclosure relates to an apparatus and a method for predicting biometrics based on a fundus image. Particularly, the present disclosure relates to an apparatus and a method for predicting biometrics such as the axial length, the fundus age, and the like, which are important for early diagnosis of ophthalmic diseases and brain diseases, using a fundus image and a deep neural network-based learning model.

Description of the Related Art

In an examination process in an ophthalmology department, a fundus image (fundus photo) is highly useful in that the fundus image is non-invasive and can be easily obtained with a basic examination. Particularly, there are advantages in that the fundus image may be taken with little effort and time even for patients who are relatively uncooperative or patients with decreased eyesight and may be easily photographed even in a state in which the pupil of a subject is not dilated.

However, in the related art, an expensive fundus imaging device was required to acquire a fundus image, but recently, there has been provided a technique capable of easily acquiring a fundus image using a lens mounted on a smartphone without an expensive device for fundus imaging.

In addition, the fundus image may be utilized to detect various retinal diseases. For example, in the diagnosis of various ophthalmic diseases such as diabetic retinopathy, retinal vein occlusion, and macular degeneration, the opinions of a specialist based on the fundus image are required.

In particular, the axial length related to the fundus condition of the patient is an important factor in evaluating the patient's condition, such as determining myopia or retinal disease. Specifically, it has been known previously that blood vessels of the retina and the choroid, the color of the background fundus, and the like are related to the axial length, but a technique capable of accurately performing numerical prediction for the axial length using this has not been known.

In addition, dedicated measuring equipment that has been developed to measure the axial length up to now corresponds to expensive and advanced equipment. In countries that cannot afford such measuring devices, or do not have developed medical infrastructure, although it is necessary to manufacture an intraocular lens of an appropriate size for the treatment of ocular diseases such as cataracts occurring in elderly patients, there is a limitation in that it is difficult to acquire detailed information on the axial length of a patient.

In addition, it is known that it is possible to determine a vascular condition of the retina from the condition of the fundus and a possibility of developing diseases related to cardiovascular diseases and brain diseases. When the fundus age that comprehensively reflects the fundus condition of the patient is calculated numerically, it is expected that a systemic blood vessel condition, a brain aging risk, and the like of the patient are inferred by comparing the actual age of the patient with the calculated fundus age to be used as an indicator for the patient's health condition.

The background art of the present disclosure is disclosed in Korean Patent Publication No. 10-2019-0087272.

SUMMARY

An object to be achieved by the present disclosure is to provide an apparatus and a method for predicting any type of biometric of a subject using his or her fundus image that can be easily captured, in the purpose of reducing any type of cost to measure the biometrics such as preparing an expensive equipment or time and space required to operate the measuring machine, and the biometrics include the axial length, the fundus age, and the like.

Objects of the present disclosure are not limited to the above-mentioned objects, and other objects, which are not mentioned above, can be clearly understood by those skilled in the art from the following descriptions.

According to an aspect of the present disclosure, there is provided a method for predicting biometrics using a fundus image including steps of preparing a plurality of learning fundus images, generating a learning model based on at least one characteristic of the fundus reflected in the prepared learning fundus images, receiving a prediction target of fundus image, and predicting the biometrics of the subject.

The biometrics may include an axial length.

At least one characteristic of the fundus reflected in the fundus images may include the shape of the choroidal vessels and the optic disc, and any condition of the fundus shown in a fundus image.

The method for predicting the biometrics based on the fundus image according to an exemplary embodiment of the present disclosure may further include producing the evidence area in a prediction target of fundus image, which indicates the contribution to the prediction of the biometrics expressed as numerical values greater than or equal to a predetermined threshold.

The method for predicting the biometrics using the fundus image according to an exemplary embodiment of the present disclosure may further include outputting emphasized evidence area in a prediction target of fundus image.

The preparation of a plurality of learning fundus images may include acquiring not only a plurality of learning fundus images as the input, a corresponding biometric data as the label to train a learning model, but also the age data of the subjects of a plurality of learning fundus images, as an additional information for the training.

The generation of the learning model may include generating a learning model for predicting the biometrics based on at least one characteristic of the fundus reflected in learning fundus images and the age information of the subjects of learning fundus images.

The reception of a prediction target of fundus image 2 may include acquiring the age data of the subject of the prediction target of fundus image 2.

A prediction of the biometrics may include predicting the axial length using the prediction target of fundus image and the age data of the subject of the prediction target of fundus image.

The biometrics may include the fundus age.

At least one characteristic of the fundus reflected in the fundus images may include at least one condition of at least one blood vessel shown in the fundus images.

According to another aspect of the present disclosure, there is provided an apparatus for predicting biometrics using a fundus image, consisting of a learning unit for preparing a plurality of learning fundus images and corresponding biometric data, generating a learning model using learning fundus images and the biometric data based on at least one characteristic of the fundus reflected in the learning fundus images, and an inference unit for receiving a prediction target of fundus image and predicting the biometrics of the subject using the generated learning model.

The apparatus for predicting the biometrics using a fundus image according to an exemplary embodiment of the present disclosure may further include a visualization unit for producing the evidence area in a prediction target of fundus image, which indicates the contribution to the prediction of the biometric expressed as numerical values greater than or equal to a predetermined threshold, and outputting the emphasized evidence area in the prediction target of fundus image.

The learning unit may acquire the age data of subjects of a plurality of learning fundus images.

The learning unit may generate a learning model for predicting the biometrics based on at least one characteristic of the fundus reflected in learning fundus images and the age information of the subjects of the learning fundus images.

The inference unit may acquire the age data of the subject of a prediction target of fundus image.

The inference unit may predict the axial length using a prediction target of fundus image and the age data of the subject of the prediction target of fundus image.

The above-mentioned aspects are merely exemplary and should not be construed as limiting the present disclosure. In addition to the above-described exemplary embodiments, additional exemplary embodiments may exist in the drawings and detailed description of the disclosure.

According to the present disclosure, it is possible to provide an apparatus and a method for predicting biometrics of a subject such as the axial length and the fundus age, using a fundus image in the purpose of reducing any type of cost to measure the biometrics such as preparing an expensive equipment or time and space required to operate the measuring machine.

According to the present disclosure, it is possible to support countries that cannot afford biometric-measuring devices or do not have developed medical industry infrastructure, by providing a simple and stable method to secure important biometrics such as an axial length and a fundus age.

According to the present disclosure, it is possible to secure the reliability of the predicted biometrics and assist accurate judgement of medical staffs who confirm the predicted biometrics by providing the emphasized evidence area expressed as numerical values indicating the degree of contribution to the prediction of the biometrics.

The effects according to the present disclosure are not limited to the contents exemplified above, and more various effects are included in the present specification.

BRIEF DESCRIPTION OF THE DRAWINGS

The above and other aspects, features and other advantages of the present disclosure will be more clearly understood from the following detailed description taken in conjunction with the accompanying drawings, in which.

DETAILED DESCRIPTION OF THE EMBODIMENT

Figure 1:
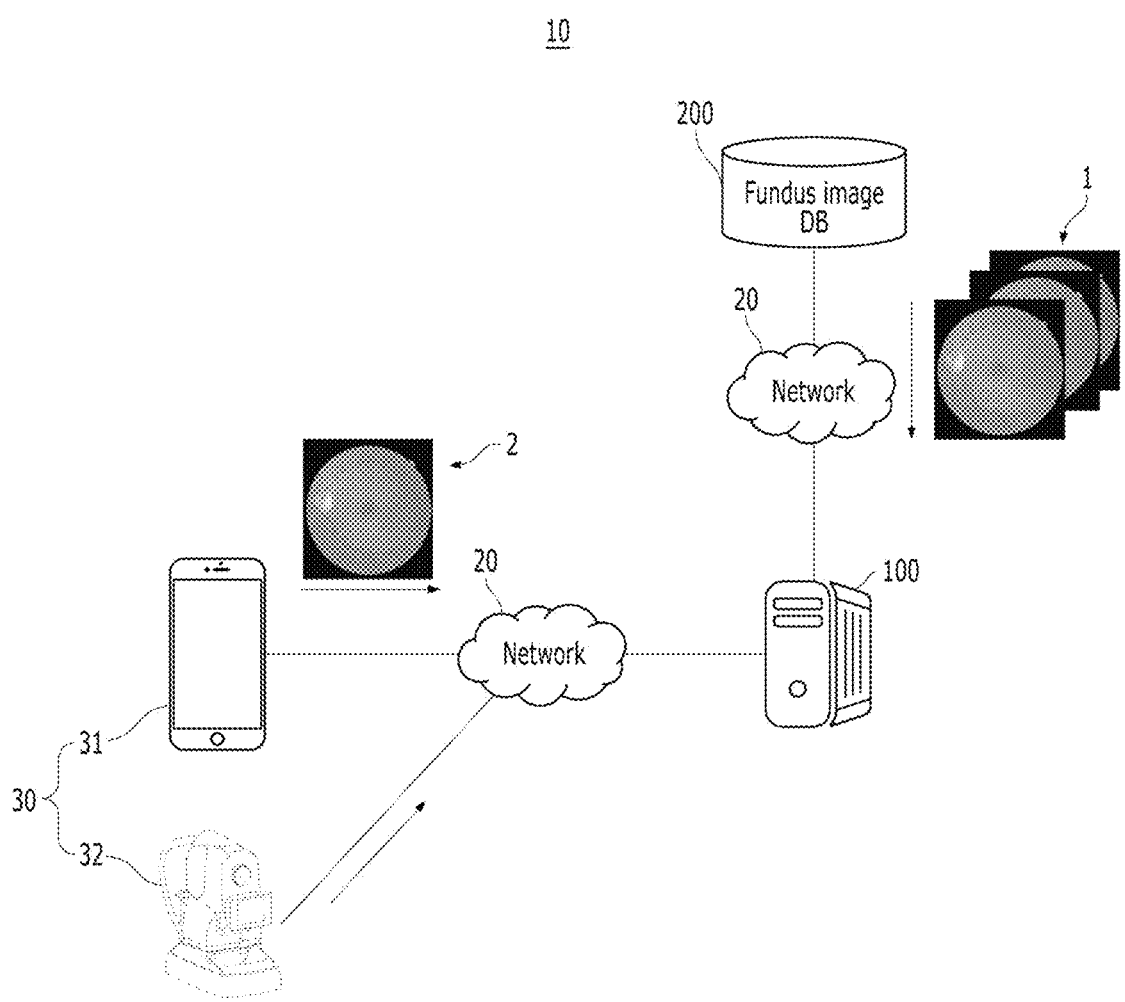
FIG. 1 is a schematic configuration diagram of a biometric system including an apparatus for predicting biometrics using a fundus image according to an exemplary embodiment of the present disclosure.

Hereinafter, exemplary embodiments of the present disclosure will be described in detail so as to be easily implemented by those skilled in the art, with reference to the accompanying drawings. However, the present disclosure may be embodied in many different forms and is not limited to the exemplary embodiments to be described herein. In addition, parts not related to the description have been omitted in order to clearly describe the present disclosure in the drawings and throughout this specification, like reference numerals designate like elements.

Further, throughout this specification, when a certain part is "connected" with the other part, it is meant that the certain part may be "directly connected" with the other part and "electrically connected" or "indirectly connected" with the other part with another element interposed therebetween.

Throughout this specification, it will be understood that when a member is referred to as being "on", "above", "at the top of", "under", "below", and "at the bottom of" the other member, it can be directly on the other member or intervening members may also be present.

Throughout this specification, unless explicitly described to the contrary, a case where any part "includes" any component will be understood to imply the inclusion of stated components but not the exclusion of any other component.

The present disclosure relates to an apparatus and a method for predicting biometrics based on a fundus image. Particularly, the present disclosure relates to an apparatus and a method for predicting biometrics such as the axial length, the fundus age, and the like which are important for early diagnosis of ophthalmic diseases and brain diseases, using a fundus image and a deep neural network-based learning model.

FIG. 1 is a schematic configuration diagram of a biometric system including an apparatus for predicting biometrics using a fundus image according to an exemplary embodiment of the present disclosure.

Referring to FIG. 1, a biometric system 10 includes an apparatus 100 for predicting biometrics using a fundus image according to an exemplary embodiment of the present disclosure (hereinafter, referred to as a 'biometric prediction apparatus 100'), a fundus image DB 200, and a fundus image photographing device 30.

The biometric prediction apparatus 100 may communicate with a fundus image DB 200 and a fundus image photographing device 30 via a network 20. The network 20 refers to a connection structure capable of exchanging information between nodes, such as terminals and servers. Examples of the network 20 include a 3rd generation partnership project (3GPP) network, a long term evolution (LTE) network, a 5G network, a world interoperability for microwave access (WiMAX) network, Internet, a local area network (LAN), a wireless local area network (Wireless LAN), a wide area network (WAN), a personal area network (PAN), a WiFi network, a Bluetooth network, a satellite broadcasting network, an analog broadcasting network, a digital multimedia broadcasting (DMB) network, and the like, but are not limited thereto.

According to the exemplary embodiment of the present disclosure, the fundus image photographing device 30 may include a user terminal 31. The user terminal 31 may include, for example, a smartphone, a SmartPad, a tablet PC, etc., and all types of wireless communication devices, such as personal communication system (PCS), global system for mobile communication (GSM), personal digital cellular (PDC), personal handyphone system (PHS), personal digital assistant (PDA), international mobile telecommunication (IMT)-2000, code division multiple access (CDMA)-2000, W-code division multiple access (W-CDMA), and wireless broadband Internet (Wibro). As another example, the fundus image photographing device 30 may include a fundus camera 32 which is provided in ophthalmology, university hospitals, etc. and is a dedicated photographing device for acquiring a fundus image of a patient.

In addition, according to the exemplary embodiment of the present disclosure, a fundus image DB 200 may be a database that can receive, send, and save a plurality of learning fundus images and any type of biometric data including the axial length and the age of subject. 2. In the description of the exemplary embodiment of the present disclosure, the 'learning fundus images and a corresponding biometric data' 1 may refer to training data used in a process of generating a learning model by the biometric prediction apparatus 100 of the present disclosure, and the 'prediction target of fundus image' 2 may refer to a fundus image data used for predicting biometrics with the generated learning model.

First, the biometric prediction apparatus 100 may prepare a plurality of learning fundus images and a corresponding biometric data 1. Specifically, the biometric prediction apparatus 100 may receive a plurality of learning fundus images and a corresponding biometric data 1, from the fundus image DB 200.

In addition, the biometric prediction apparatus 100 may adjust the data distribution of the plurality of received learning fundus images and the corresponding biometric data 1 to prevent overfitting when implementing a learning model to be described below. In other words, the biometric prediction apparatus 100 selects some of the plurality of received learning fundus images and the corresponding biometric data 1 based on a predetermined criteria, and the selected learning fundus images and the corresponding biometric data 1 may be used for training a learning model.

According to the exemplary embodiment of the present disclosure, the plurality of learning fundus images and the corresponding biometric data 1 may include the corresponding age data as an additional data used for training a learning model for predicting the axial length, and all the mentioned data can be pre-stored in the fundus image 200. In other words, when the biometric prediction apparatus 100 receives a plurality of learning fundus images and the corresponding axial length data as the label to train a learning model which predicts the axial length, the biometric prediction apparatus 100 may acquire, the age data of the subjects as an additional information for the training.

After training a learning model, the biometric prediction apparatus 100 can collect an additional plurality of learning fundus images and the corresponding axial length data 1 based on the errors in predictions of the learning model, and re-train the learning model with the newly collected data to increase the performance in certain prediction region.

In addition, the biometric prediction apparatus 100 may generate a learning model based on at least one characteristic of the fundus reflected in learning fundus image. In addition, the biometric prediction apparatus 100 may generate a learning model based on at least one characteristic of the fundus reflected in learning fundus image, and the age information of the subjects of the plurality of learning fundus images according to the exemplary embodiment of the present disclosure.

Here, the biometrics may include the axial length (AL). In other words, the biometric prediction apparatus 100 may generate a learning model for predicting the axial length of a subject using his or her fundus image.

According to the exemplary embodiment of the present disclosure, referring to FIG. 1, the biometric prediction apparatus 100 may receive a plurality of prediction target of fundus image 2 from the fundus image photographing device 30, but is not limited thereto. As another example, the biometric prediction apparatus 100 may be mounted (installed) on the user terminal 31 in the form of an application. At this time, the biometric prediction apparatus 100 has the learning model disclosed herein through self-edge learning in the user terminal 31 which is an edge device. Even if the prediction target of fundus image 2 taken at the user terminal 31 cannot be transmitted to a separate server or computing device via the network, the biometric prediction apparatus 100 may operate to output predicted biometrics at the user terminal 31.

In addition, the biometric prediction apparatus 100 may acquire the age data of the subject of a prediction target of fundus image 2 when receiving a prediction target of fundus image 2. In addition, the biometric prediction apparatus 100 may predict the axial length using the acquired prediction target of fundus image 2 and the age data of the subject of a prediction target of fundus image 2. As such, when the age data of the subject of a prediction target of fundus image 2 is secured, a correlation between the age and the axial length may be additionally considered, so that a prediction result of the axial length may be more accurate.

Figure 2:
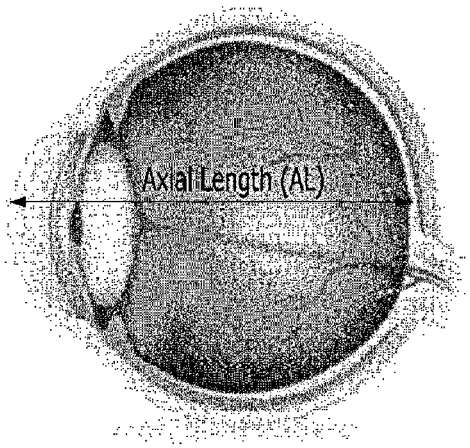
FIG. 2 is a schematic diagram for describing the axial length.

FIG. 2 is a schematic diagram for describing the axial length.

Referring to FIG. 2, the axial length may refer to a distance from the cornea of to the center of the macula (central fovea).

In this regard, when the biometric prediction apparatus 100 uses the axial length as the biometrics to be predicted, specifically, the learning model generated by the biometric prediction apparatus 100 may be constructed to predict the axial length, based on the shapes of the choroidal vessels and the optic disc which are characteristics of the fundus reflected in learning fundus image.

Figure 3:
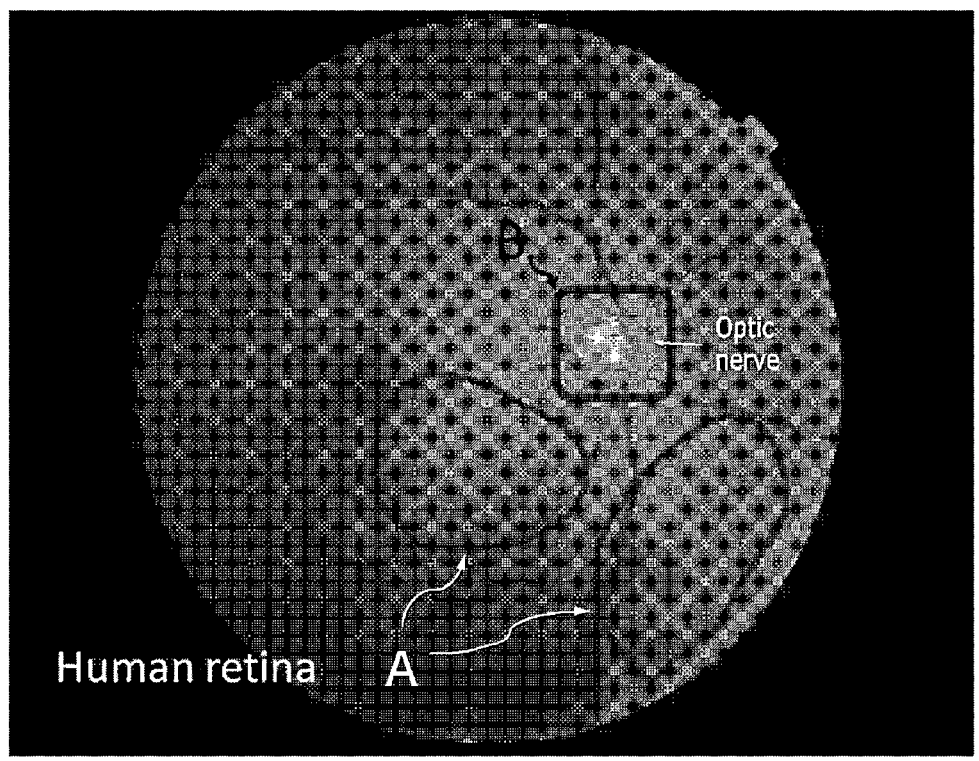
FIG. 3 is a schematic diagram for describing the shape of the choroidal vessels and the optic disc, which are characteristics of the fundus in a fundus image used for the biometric predictions.

FIG. 3 is a schematic diagram for describing the shape of choroidal vessels and the optic disc, which are characteristics of the fundus in a fundus image considered to predict biometrics.

In particular, FIG. 3A shows an example of the shape of choroidal vessels, which is one of the characteristics of the fundus in the fundus image, and FIG. 3B may illustrate an example of the shape of the optic disc which is one of characteristics of the fundus in the fundus image.

Specifically, the shape of choroidal vessels may mean the choroidal vessels reflected in a fundus image. In this regard, generally, as the axial length is increases, the choroidal vessel area may be significantly shown in a fundus image, and as the age of the subjects increases, a larger choroidal vessel area may be shown in the fundus image, which is associated with a pigment decrease of the choroid and the thinning process of retina. In other words, the better the choroidal vessels are observed in a fundus image, the higher the age of the subject or the longer the axial length of the subject can be judged.

That is, when a learning model constructed using a plurality of learning fundus images and a corresponding biometric data 1 receives a prediction target of fundus image 2, the learning model may output longer axial length as the choroidal vessels in the prediction target of fundus image 2 are well observed or the area of the choroidal vessels is significantly large in the prediction target of fundus image 2.

In addition, the characteristics of the optic disc, where the optic nerves of the retina are collected and the axon of ganglion cells exits the retina, may include the optic disc tilt, the position (coordinates in the image) of the optic disc, the distance from the fovea, any shape information such as radius, diameter, and edge length of the optic disc area, the lamina cribrosa thickness, the prelaminar tissue thickness, and anterior laminar displacement of the optic disc, and the like, which are reflected in the fundus image.

In addition, according to the exemplary embodiment of the present disclosure, the biometrics may include the fundus age. In other words, the biometric prediction apparatus 100 may generate a learning model for predicting the fundus age of the subject using the fundus images and the corresponding age data.

In the description of the exemplary embodiment of the present disclosure, the fundus age means the age of a subject to be predicted using his or her fundus image, and may be used as an index that comprehensively reflects the eye health condition such as the condition of blood vessels in the fundus, and the like of the subject inferred from the fundus image. Accordingly, as described below, the fundus age may be used to evaluate the health condition of a subject or to diagnose (determine) the presence or absence of a disease in a subject by comparing the actual age of the subject and the predicted fundus age.

Specifically, when the fundus age of a subject predicted by the biometric prediction apparatus 100 using the received prediction target of fundus image 2 is lower than the actual age of the subject, it is determined that the eye health condition or systemic blood vessel condition of the subject is good. However, conversely, when the predicted fundus age is higher than the actual age of the subject, it may infer that the eye health condition or systemic blood vessel condition of the subject is abnormal.

In this regard, when the biometric prediction apparatus 100 uses the fundus age as a biometric to be predicted, specifically, a learning model generated by the biometric prediction apparatus 100 may be constructed to predict the fundus age based on at least one condition of the fundus reflected in learning fundus images. Here, at least one condition of the fundus may include the information of the distribution, thickness, and color of the blood vessels shown in the fundus image, and the information of the color and contrast of the background of the fundus.

According to the exemplary embodiment of the present disclosure, the biometric prediction apparatus 100 may construct a deep neural network (DNN)-based learning model as the learning model for predicting the biometrics. The biometric prediction apparatus 100 may construct a learning model by referring to existing models such as LeNet, AlexNet, GoogleNet, VGGNet, ResNet, etc., which are deep neural network models for image processing, but is not limited thereto. Illustratively, the type of learning model disclosed herein may be ResNet-18.

Figure 4:
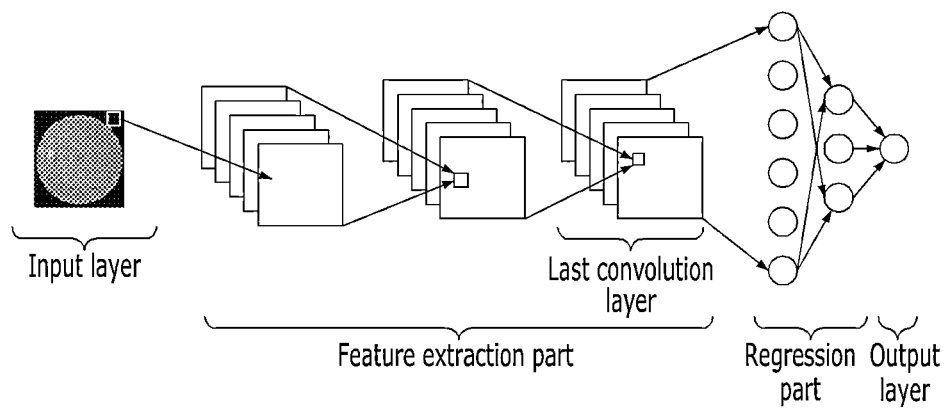
FIG. 4 is a schematic diagram for describing a deep neural network-based learning model according to an exemplary embodiment of the present disclosure.

FIG. 4 is a schematic diagram for describing a deep neural network-based learning model according to an exemplary embodiment of the present disclosure.

Referring to FIG. 4, the deep neural network-based learning model according to an exemplary embodiment of the present disclosure is a multi-layered network, and consists of four parts: the input layer, the feature extraction part composed of convolution layers, regression part composed of fully connected layers, and the output layer.

In this case, the number of nodes in the input layer may be the dimension of a fundus image to input, and the number of nodes in the output layer may be the dimension of a biometric data. That is, the number of input nodes for a learning model constructed by the biometric prediction apparatus 100 disclosed herein may be the number of pixels of the fundus image, and the number of output nodes may be one because a value of the axial length or a value of the fundus age is scalar.

A convolution layer is a layer that calculates the correlation between the local characteristics of the input image (the characteristics of a local area) and the specific patterns, and the feature extraction part may consist of multiple convolution layers, and properties of each convolution layer may be the number of filters, stride and type of convolution operation. As such, in the feature extraction part consisting of multiple convolution layers, the level of abstraction is determined according to the number of convolution layers, and as the number of layers increases (in other words, as the layers get deeper), detailed features may be extracted from the input image, generally. According to the exemplary embodiment of the present disclosure, in order to improve efficiency and accuracy of extracting local characteristics, multiple convolution layers can be connected in parallel or sequential, and any other options for setting a feature extraction part may be additionally provided. In addition, pooling, a nonlinear filter, and the like that extract only necessary values between convolution layers may be applied to reduce noise or unnecessary signal from the previous step.

Based on the feature vectors extracted from a feature extraction part, in the regression part, multiple fully connected layers may be sequentially connected, ending with a node that finally outputs a predicted value (scalar or result value), after performing regression through the multiple fully connected layers.

In addition, the biometric prediction apparatus 100 may produce the evidence area in a prediction target of fundus image 2, where each point has a numerical value equal to or greater than a predetermined threshold, indicating the degree of contribution to the prediction of biometrics (e.g., axial length, fundus age, etc.).

In addition, the biometric prediction apparatus 100 may output (display) the emphasized evidence area in a prediction target of fundus image 2. For example, the biometric prediction apparatus 100 makes the color, contrast, sharpness, etc. of the produced evidence area distinguished from the background areas in a prediction target of fundus image 2, so that users (medical staff, etc.) can visually identify or recognize the evidence area promptly.

In addition, according to the exemplary embodiment of the present disclosure, as the change of the calculated values of points (pixels) in an emphasized evidence area is abrupt, the changes in hue, brightness, and saturation of the pixels can be made significant.

Figure 5:
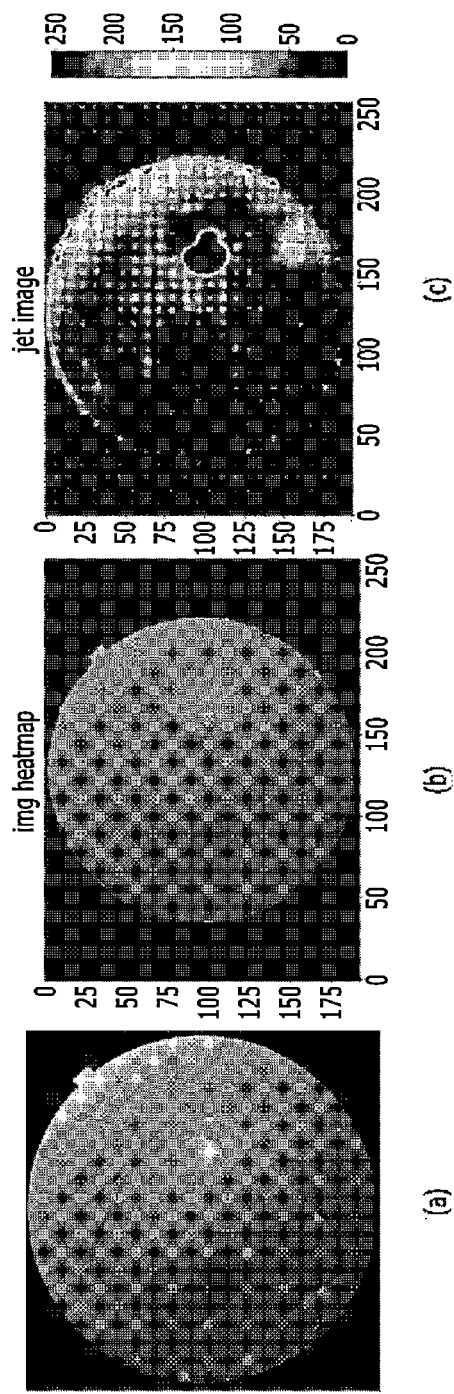
FIG. 5 is a diagram exemplarily illustrating an output of the emphasized evidence area in a prediction target of fundus image, and each point in the emphasized evidence area has a numerical value equal to or greater than a predetermined level, indicating the degree of contribution to the prediction of biometric.

FIG. 5 is a diagram exemplarily illustrating an output of the emphasized evidence area in a prediction target of fundus image 2, where each point in the emphasized evidence area has a numerical value equal to or greater than a predetermined threshold, indicating the degree of contribution to the prediction of biometric.

According to the exemplary embodiment of the present disclosure, the biometric prediction apparatus 100 applies a differential operation to the output with respect to the nodes in the input layer or the nodes of the last layer of the feature extraction part to evaluate the contribution to the predicted value of biometrics.

In particular, FIG. 5A exemplarily illustrates a prediction target of fundus image 2, FIG. 5B exemplarily illustrates a prediction target of fundus image 2 with the emphasized evidence area after calculating the evidence area by an application of differentiation of the output with respect to the input, and FIG. 5C exemplarily illustrates a prediction target of fundus image 2 with the emphasized evidence area after calculating the evidence area using an application of differentiation of the output with respect to the nodes of the last convolutional layer of the feature extraction part. In addition, according to the exemplary embodiment of the present disclosure, FIG. 5C illustrating an example of the emphasized evidence area in a prediction target of fundus image 2 may be referred to as saliency map, class activation map (CAM), and gradient-class activation map (Grad-CAM), and the like depending on the method used.

Hereinafter, with reference to Equations 1 to 4, an exemplary embodiment in which the biometric prediction apparatus 100 produces the evidence area in a prediction target of fundus image 2 will be described in detail.

Using a backpropagation algorithm, the parameters of a deep neural network-based learning model described in FIG. 4 can be optimized, and a trained learning model can be used for producing the estimates of the biometrics (e.g., axial length, fundus age, etc.) as well as the evidence area computed by differentiating the output (the estimates) with respect to the nodes of the input layer, or with respect to the nodes of the last layer of the feature extraction part.

Specifically, when a learning model is a deep neural network consisting of n fully connected layers in the regression part, and m convolutional layers in the feature extraction part, the learning model may be defined as a function in a specific function space as shown in Equation 1 below.

$$Y = f_{fC_n} \cdots f_{fC_2} f_{fC_1}(f_{CV_m} \cdots f_{CV_2} f_{CV_1}(X_{input})) \quad \text{[Equation 1]}$$

In addition, it is possible to know which nodes are important in predictions that a neural network-based learning model makes, by observing a change in the value of the output node according to a change in the value of a node of interest, which may be a part of calculating the degree of contribution to the output for each node, and this calculation may be a part of a process for obtaining the evidence area using the input layer or the last layer in the feature extraction part as expressed in Equation 2 to 4 below.

$$X' = f_{CV_m} \cdots f_{CV_2} f_{CV_1}(X_{input}) \quad \text{[Equation 2]}$$

In addition, it is possible to obtain the derivative of the output numerically with respect to a specific node, $X'_{k,i,j}$, at i'th row and j'th column of the k'th channel, $X'_k$, among the channels (filters) in the layer, $X'$, and it could be a way to numerically calculate the degree of contribution to the output for a node of specific channel in a layer, by multiplying the obtained differential value as a weight by the value of the node. In addition, it could be a way to numerically calculate the degree of contribution of to the output for the nodes at the same coordinate of channels in a layer, by adding all calculated contributions of the nodes, and, in this way, it is possible to evaluate the contribution that an area, which is made up of multiple nodes in the last convolution layer of the feature extraction part, makes to the prediction of a learning model, as expressed in Equation 3 below.

$$Y_{reason,i,j} = W_{i,j} \cdot X'_{i,j}, \quad \text{[Equation 3]}$$

$$W_{i,j} = \frac{\partial Y}{\partial X'_{i,j}}$$

$$Y_{reason,i,j} = \sum_k W_{k,i,j} \cdot X'_{k,i,j}$$

where k is the index of the channels to the last later of the feature extraction part.

In addition, in relation to the producing the evidence area using the input layer, the derivative of the output with respect to the nodes in the input layer may be used as a weight when calculating the degree of contribution to the output, and a possible form is expressed in Equation 4 below.

$$Y_{reason,i,j} = \sum_{input} W_{input,i,j} \cdot X'_{input,i,j} \quad \text{[Equation 4]}$$

As such, the biometric prediction apparatus 100 disclosed herein produces the evidence area where the degree of the contribution to a prediction and display with an emphasis, thereby securing the reliability of the predicted biometrics (e.g., axial length, fundus age, etc.) and assisting the accurate decision of medical staffs who confirm the predictions.

Figure 6:
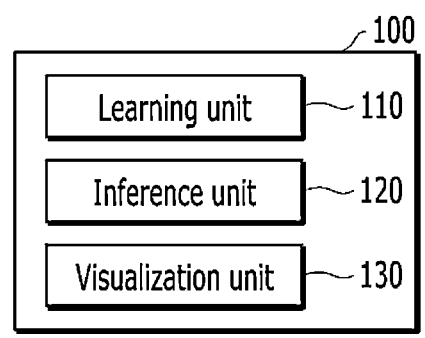
FIG. 6 is a schematic configuration diagram of an apparatus for predicting biometrics using a fundus image according to an exemplary embodiment of the present disclosure.

FIG. 6 is a schematic configuration diagram of an apparatus for predicting biometrics using a fundus image according to an exemplary embodiment of the present disclosure.

Referring to FIG. 6, the biometric prediction apparatus 100 may include a learning unit 110, an inference unit 120, and a visualization unit 130.

The learning unit 110 may prepare a plurality of learning fundus images and a corresponding biometric data 1. In addition, the learning unit 110 may acquire the age data of the subjects of a plurality of learning fundus images.

In addition, the learning unit 110 may generate a learning model using the prepared fundus images and the corresponding biometric data, based on at least one characteristic of the fundus reflected in the prepared plurality of learning fundus images. In addition, the learning unit 110 may use the age data as an additional information for generating a learning model which predicts biometrics based on at least one characteristic of the fundus reflected in the plurality of learning fundus images. In other words, the learning unit 110 may train a learning model using not only the plurality of learning fundus image and the corresponding biometric data 1 as the input and the label, but also the age data as an additional information of the subject of the plurality of learning fundus images.

Here, the biometrics may include the axial length and the fundus age. In addition, at least one characteristic of the fundus reflected in a fundus image may include the shape of the choroidal vessels and the optic disc, and any condition of the fundus shown in a fundus image.

The inference unit 120 may receive a prediction target of fundus image 2. In addition, the inference unit 120 may acquire the age data of the subject of a prediction target of fundus image 2.

In addition, the inference unit 120 may predict biometrics of the subject using a prediction target of fundus image 2 and the learning model generated by the learning unit 110. In addition, the inference unit 120 may predict the axial length using a prediction target of fundus image 2 with the age data of the subject of the prediction target of fundus image 2.

The visualization unit 130 may produce the emphasized evidence area in a prediction target of fundus image 2, where each point in the emphasized evidence area has a numerical value equal to or greater than a predetermined threshold, indicating the degree of contribution to the prediction of biometric.

According to the exemplary embodiment of the present disclosure, the visualization unit 130 may display an image (e.g., saliency map, CAM (Class activation map), Grad-CAM (gradient-class activation map), etc. that may be understood through FIG. 5C) showing the emphasized evidence area in a prediction target of fundus image 2 itself or together with the prediction target of fundus image 2 (e.g., displayed in parallel horizontally or vertically), but the present disclosure is not limited thereto. As another example, the visualization unit 130 may provide multiple modes for displaying the emphasized evidence area in a prediction target of fundus image 2, and may operate to switch each mode according to an input to the biometric prediction apparatus 100.

Hereinafter, an operational flow of the present disclosure will be briefly described based on the contents described above in detail.

Figure 7:
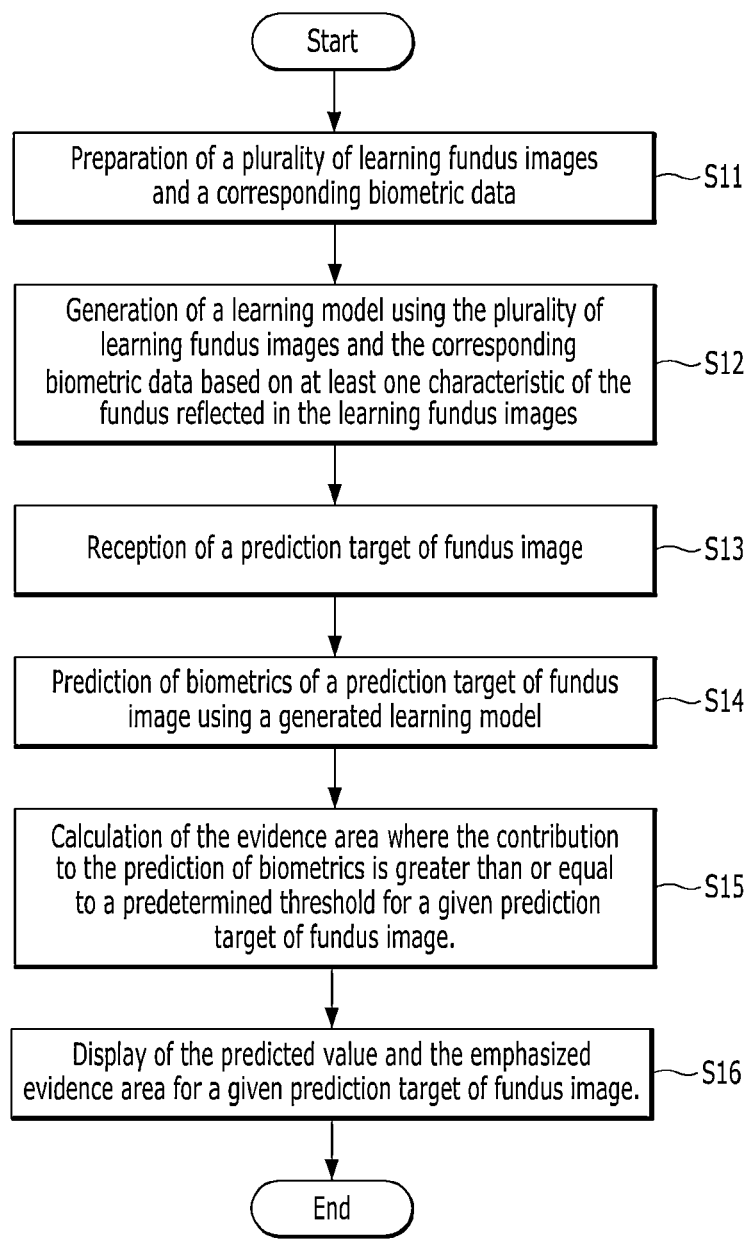
FIG. 7 is an operation flowchart of a method for predicting biometrics using a fundus image according to an exemplary embodiment of the present disclosure.

FIG. 7 is an operation flowchart of a method for generating a learning model with fundus images and corresponding biometric data, and predicting biometrics using a fundus image according to an exemplary embodiment of the present disclosure.

The method for predicting biometrics using a fundus image illustrated in FIG. 7 may be performed by the biometric prediction apparatus 100 described above. Accordingly, even if omitted below, the contents described for the biometric prediction apparatus 100 may be equally applied to the description of the method for predicting biometrics using a fundus image.

Referring to FIG. 7, in step S11, the learning unit 110 may prepare a plurality of learning fundus images and a corresponding biometric data 1.

In addition, in step S11, the learning unit 110 may acquire a plurality of learning fundus images and a corresponding biometric data 1 and the age data of the subjects of a plurality of learning fundus images.

In addition, in step S12, the learning unit 110 may generate a learning model using the prepared plurality of learning fundus images and the corresponding biometric data 1 as the input and the label, based on at least one characteristic of the fundus reflected in the prepared plurality of learning fundus images.

In addition, in step S12, the learning unit 110 may generate a learning model for predicting biometrics based on at least one characteristic of the fundus reflected in the fundus image, and the age information of the subjects the prepared plurality of learning fundus images.

Next, in step S13, the inference unit 120 may receive a prediction target of fundus image 2.

In addition, in step S13, the inference unit 120 may receive the age data of the subject of a prediction target of fundus image 2.

In addition, in step S14, the inference unit 120 may predict biometrics of the subject using his or her prediction target of fundus image 2 and a learning model generated in step S12.

In addition, in step S14, the inference unit 120 may predict an axial length as a biometric using the prepared prediction target of fundus image 2 with age data of the subject of a prediction target of fundus image 2 acquired in step S11.

Next, in step S15, the visualization unit 130 may produce the evidence area where each point (pixel) in the evidence area has a value equal to or greater than a predetermined threshold, indicating the degree of contribution to the prediction of biometrics.

Next, in step S16, the visualization unit 130 may output the emphasized evidence area in a prediction target fundus image 2 after producing the evidence area in step S15.

In the above description, steps S11 to S16 may be subdivided into more steps or may be merged into fewer steps according to an exemplary embodiment of the present disclosure. In addition, some steps may also be omitted if necessary, or the order between the steps may also be changed.

The method for predicting biometrics based on a fundus image according to the exemplary embodiment of the present disclosure may be implemented in a form of program instructions which may be performed through various computer means to be recorded in a computer readable medium. The computer readable medium may include program instructions, data files, data structures, and the like alone or in combination. The program instructions recorded in the medium may be specially designed and configured for the present disclosure, or may be publicly known to and used by those skilled in the computer software art. Examples of the computer readable medium include magnetic media, such as a hard disk, a floppy disk, and a magnetic tape, optical media such as a CD-ROM and a DVD, magneto-optical media such as a floptical disk, and hardware devices such as a ROM, a RAM, and a flash memory, which are specially configured to store and execute the program instructions. Examples of the program instructions include high language codes executable by a computer using an interpreter and the like, as well as machine language codes created by a compiler. The hardware device may be configured to be operated with one or more software modules in order to perform the operation of the present disclosure and vice versa.

Further, the aforementioned method for predicting biometrics using a fundus image may be implemented even in a form of computer programs or applications to be executed by a computer, which are stored in the recording medium.

The aforementioned description of the present disclosure is to be exemplified, and it can be understood by those skilled in the art that the technical spirit or required features of the present disclosure can be easily modified in other detailed forms without changing. Therefore, it should be appreciated that the embodiments described above are illustrative in all aspects and are not restricted. For example, respective components described as single types can be distributed and implemented, and similarly, components described to be distributed can also be implemented in a coupled form.

The scope of the present disclosure is represented by claims to be described below rather than the detailed description, and it is to be interpreted that the meaning and scope of the claims and all the changes or modified forms derived from the equivalents thereof come within the scope of the present disclosure.

What is claimed is:

1. A method for predicting biometrics using a fundus image comprising following steps:
   preparing a plurality of learning fundus images and a biometric data corresponding to each of the learning fundus images, the biometric data including an axial length;
   generating a learning model for predicting corresponding biometrics using the learning fundus images and the biometric data, based on at least one characteristic of a fundus reflected in the learning fundus images, the at least one characteristic of the fundus including at least one of a shape of choroidal vessels and an optic disc;
   receiving a fundus image data of a prediction target subject; and
   predicting biometrics for the prediction target subject by using the learning model.

2. The method for predicting biometrics according to claim 1, further comprising:
   producing an evidence area expressed as a numerical value greater than or equal to a predetermined threshold, which represents a degree of contribution to the predicting.

3. The method for predicting biometrics according to claim 2, further comprising:
   outputting and visualizing the evidence area with an emphasis.

4. The method for predicting biometrics according to claim 1, wherein the preparing includes:
   acquiring an age data of a subject corresponding to each of the learning fundus images, and
   the generating includes: generating a learning model for predicting biometrics using the learning fundus images, the biometric data and the age data.

5. The method for predicting biometrics according to claim 4, wherein the receiving includes: acquiring an age information of the prediction target subject, and
   the predicting includes: predicting an axial length of the prediction target subject.

6. The method for predicting biometrics according to claim 4, wherein the biometric data includes a fundus age, and
   the predicting includes: predicting a fundus age of the prediction target subject.

7. The method for predicting biometrics according to claim 6, further comprising:
   comparing the fundus age of the prediction target subject and the age information of the prediction target subject to evaluate a health condition of the prediction target subject or diagnose a presence of disease in the prediction target subject.

8. A non-transitory computer readable recording medium which records programs for executing the method of claim 1.

9. A non-transitory computer readable recording medium which records programs for executing the method of claim 2.

10. A non-transitory computer readable recording medium which records programs for executing the method of claim 3.

11. A non-transitory computer readable recording medium which records programs for executing the method of claim 4.

12. A non-transitory computer readable recording medium which records programs for executing the method of claim 5.

13. A non-transitory computer readable recording medium which records programs for executing the method of claim 6.

14. A non-transitory computer readable recording medium which records programs for executing the method of claim 7.

* * * * *